United States Patent [19]

Shukla et al.

[11] Patent Number: 5,968,831
[45] Date of Patent: *Oct. 19, 1999

[54] CELL CONTROL USED TO CONFIRM ENZYMATIC ACTIVITY

[75] Inventors: Ravindra S. Shukla; Harold R. Crews, both of Pembroke Pines; Adry Galiounghi; Eileen Landrum, both of Miami; Frank J. Lucas, Boca Raton, all of Fla.

[73] Assignee: Coulter International Corp., Miami, Fla.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/739,362

[22] Filed: Oct. 29, 1996

[51] Int. Cl.$^6$ .............................. G01N 31/00; C12Q 1/00; C12Q 1/34; C12N 5/08
[52] U.S. Cl. ................................ 436/8; 436/63; 436/172; 435/4; 435/18; 435/40.5; 435/372
[58] Field of Search .................. 435/1.1, 2, 6, 7.1, 435/7.21, 7.4, 195, 374, 4, 18, 40.5, 372; 436/8, 63, 172

[56] References Cited

U.S. PATENT DOCUMENTS

| | | | |
|---|---|---|---|
| 5,032,381 | 7/1991 | Bronstein et al. | 435/4 |
| 5,059,518 | 10/1991 | Kortright et al. | 435/6 |
| 5,178,884 | 1/1993 | Goodrich et al. | 424/533 |
| 5,443,986 | 8/1995 | Haughland et al. | 435/4 |

OTHER PUBLICATIONS

Dolbeare, Modern Fluorescence Spectroscopy 3, ed., E.L. Wehry, Plenum Press, NY, Chapter 6, pp. 251–293, 1981.
Lakowicz, Principles of Fluorescence Spectroscopy, Plenum Press, NY, Chapter 1, pp. 1 and 15–18, and Chapter 2, pp. 19 and 20, 1983.
ATCC Catalogue of Cell Lines and Hybridomas, 6th Edition, pp. 69, 70, 132, and 152, 1988.

*Primary Examiner*—Jon P. Weber
*Assistant Examiner*—Janet M. Kerr
*Attorney, Agent, or Firm*—Mitchell E. Alter

[57] ABSTRACT

The invention provides a cell control product for use with a cytoenzymology assay to confirm enzymatic activity in devices employing electronic and/or optical means. The cell control product comprises a lyophilized mammalian cell which is capable of being rehydrated in water to exhibit cellular structure and cellular enzymatic activity so that said lyophilized cells can function effectively as a cytoenzymology cell control in an enzymatic analysis. The cellular structure of the cell control is capable of being authenticated by light scatter or microscopy analysis and the cellular enzymatic activity is capable of being authenticated by fluorescence analysis. The cell control exhibits a real time stability when stored at between 2 and 8° C. for at least a two month period of time. Preferably the mammalian cell is an abnormal cell selected from Molt 4, CCRF-CEM and HL-60 cell lines.

6 Claims, 3 Drawing Sheets

CELL CONTROL USED TO CONFIRM ENZYMATIC ACTIVITY

FIELD OF INVENTION

This invention relates to a reference cell control made from a blood cell which is used to confirm enzymatic activity in devices employing electronic and/or optical means and processes for making and using the cell control.

BACKGROUND OF THE INVENTION

Cytoenzymology is the study of cellular enzyme function. Historically, the study of enzymatic activity of cells was pursued using cytosols. However, new reagents have been developed which are used to study enzymatic activity inside metabolically active whole cells. These new reagents have enabled cytoenzymology to advance to the stage where functional cell assays are possible to diagnose diseases and monitor therapeutic progress of such diseases by cytological examination under a microscope or by a flow cytometer. The new reagents that have been developed are synthetic fluorogenic substrate reagents that are available to measure enzyme activity inside the cellular structure. Examples of such fluorogenic substrate reagents are CELLPROBE reagents sold by Coulter Corporation, Miami, Fla. A further description of these new reagents are described in co-pending U.S. Pat. No. 5,776,720.

To determine the efficacy of a fluorogenic substrate reagent in the measurement of specific cellular enzyme activity, it is necessary to establish the efficacy of the reagent by an independent biological control material. The biological control material, also known as a cell control, is essential for determining the accuracy and precision of clinical and cytoenzymology assays. The cell control is needed to insure reliability and accuracy of test results and methods, and to insure reproducibility through time and from laboratory to laboratory. In addition, some state and federal regulations, which govern such assays, often require the use of a cell control in order to demonstrate that equipment is performing properly. The cell control should be stable and similar in nature to the sample under investigation.

U.S. Pat. No. 5,059,518 discloses a cell control, CYTO-TROL® made by Coulter Corporation, which consists of normal human cells that have been lyophilized in a hypertonic, trehalose containing media. The product is used as an antigen control in flow cytometry. The product is made from a depleted preparation of leukocytes wherein the lymphocytes are the only remaining white blood cells. However, this product does not retain enzymatic activity characteristic of normal human cells.

SUMMARY OF THE INVENTION

This invention relates to an enzymatic cell control for use in instruments employing electronic and/or optical means. The invention is further related to a cell control which is a stable lyophilized material from whole cells having intracellular activity of selected enzymes similar to human white blood cells.

The invention provides a novel cell control product comprising a lyophilized mammalian cell which is capable of being rehydrated in water to exhibit cellular structure and cellular enzymatic activity so that said lyophilized cells can function effectively as a cytoenzymology cell control in an enzymatic analysis, said cellular structure capable of being authenticated by light scatter or microscopy analysis and said cellular enzymatic activity capable of being authenticated by fluorescence analysis. The lyophilized cell control exhibits a real time stability when stored at between 2 and 8° C. for at least a two-month period of time.

The method of using a cytoenzymology cell control comprises rehydrating a lyophilized mammalian cell which is capable of being rehydrated in water to exhibit cellular structure and cellular enzymatic activity so that said lyophilized cells can function effectively as a cytoenzymology cell control in an enzymatic analysis, said cellular structure capable of being authenticated by light scatter or microscopy analysis and said cellular enzymatic activity capable of being authenticated by fluorescence analysis; placing said cell control in an instrument capable of detecting fluorescence intensity; and analyzing said cell control for fluorescence intensity.

The method of making a cytoenzymology control cell comprises collecting a sample having a predetermined number of abnormal mammalian cells suspended in a selected volume of a physiologically acceptable buffer solution; subjecting the cell suspension to centrifugation to obtain a cell pellet; adding the cell pellet to a carbohydrate solution to form a lyophilizable cell suspension; introducing the lyophilizable cell suspension to a vessel; and lyophilizing said lyophilizable cell suspension. Preferably, the abnormal mammalian cells are selected from Molt 4, CCRF-CEM and HL-60 cell lines.

DETAILED DESCRIPTION OF THE INVENTION

Figure 1A:
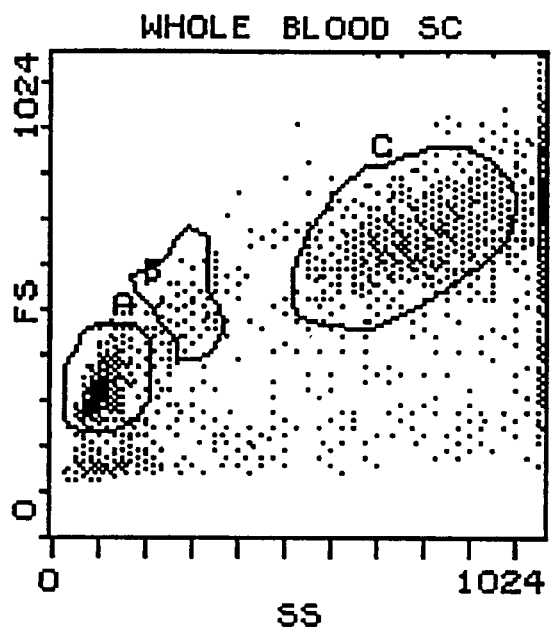
FIGS. 1, 2 and 3 represent histograms of a cell control of this invention, CYTO-TROL®, and human lymphocytes reacted with a fluorogenic substrate.
Figure 1B:
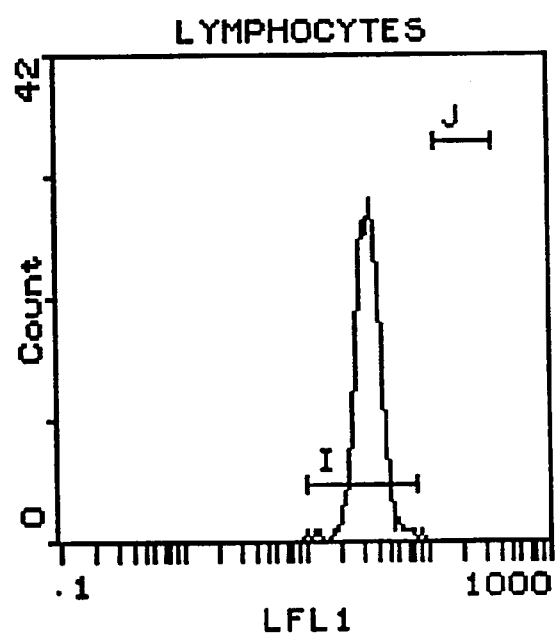
Figure 2A:
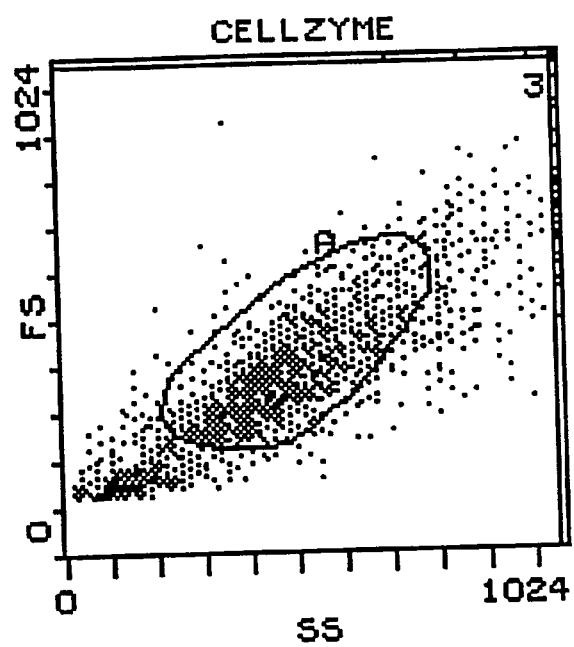
Figure 2B:
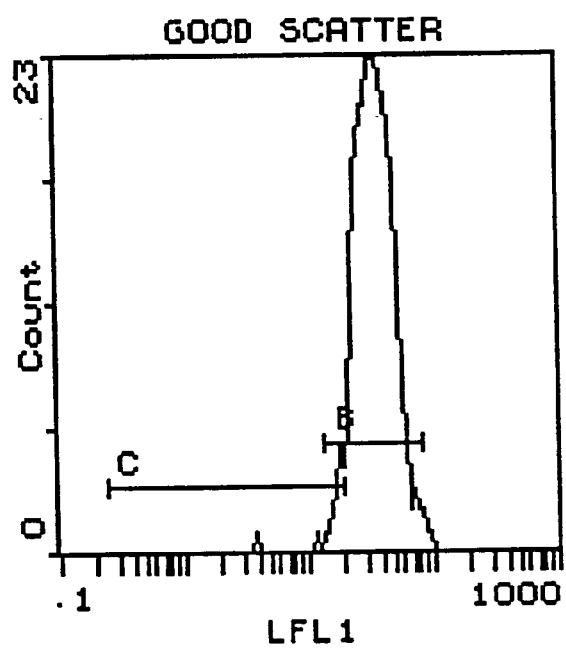
Figure 3A:
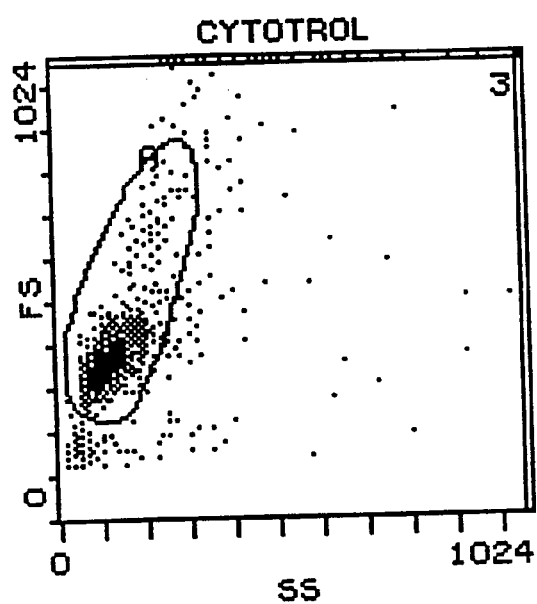
Figure 3B:
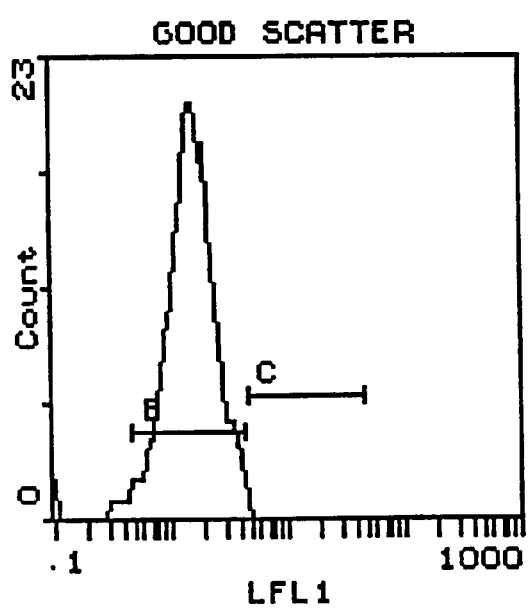

Certain terminology can be employed to explain this invention and the results of comparison tests represented by the histograms depicted in FIGS. 1 through 3. These terms as used herein are defined as follows:

1. "Background fluorescence" will refer to the fluorescent glow emanating from any material in a sample other than the specific fluorescent cell under study.
2. "Autofluorescence" is one type of background fluorescence wherein the fluorescent glow emanating from a cell is induced by other than a fluorescent chemical, such as a dye.
3. "Non-specific fluorescence" will refer to the phenomenon of a fluorescent compound being activated by a means other than by one or more enzymes in the same class contained within the cell wall.
4. "Light scatter" will refer to the phenomenon occurring in a flow cytometer instrument when an incident beam, such as from a laser source, impinges against a cell and some of the beam is reflected in a multitude of directions and some traverses through the cell. The light scattered, including its angle of reflection and the fluorescence engendered by reason of the fluorescent chemical contained within a cell, can be detected and measured for determining cell characteristics such as cell size or volume, cell surface smoothness and number of granules and other characteristics of a cell. Those characteristics are comparable with those of a normal cell.
5. "Mean Channel (MC)" means the average relative amount of fluorescence for the cells analyzed.
6. "Percent positive" means the percentage of analyzed cells which fluoresce more than the background fluorescence.
7. "Abnormal cell sample" refers to a cell sample in which the intracellular enzyme activity differs from that of a normal blood sample; or there is present an enzyme activity in the cell sample which is not present in a normal blood cell sample.

In general, the method of making a cytoenzymology control cell depends upon the selection of a cell sample which will have a selected enzyme activity after being processed. The cell sample can be prepared from leukocyte-rich, anti-coagulated blood or from a selected type of cultured cells. Preferably, the cell sample will comprise an abnormal cell sample in which the intracellular enzyme activity differs from that of a normal blood sample; or there is present an enzyme activity in the cell sample which is not present in a normal blood cell sample.

In a first instance, a cell sample of leukocytes is prepared by lysing red blood cells from a white blood cell sample and the lysis debris removed by washing. Alternatively, red blood cells may be removed by other suitable means such as the use of sedimentation techniques or an erythrocyte specific antibody conjugated to an insoluble substrate. If desired, specific types of non-erythrocyte cells can also be removed from the blood sample by the use of additional selective antibodies conjugated to insoluble supports. For example, a monoclonal antibody specific to an antigen present only on granulocytes could be conjugated to an insoluble support and the resulting conjugated antibody used to remove granulocytes from an erythrocyte-free blood sample. Glass, ceramic or polymeric beads, either magnetic or non-magnetic, are among the many types of supports which may be used. Alternatively, selected cells may also be removed by the use of well known density gradient techniques.

In a second instance, an abnormal cell sample can be prepared by the same method previously described except starting with an abnormal blood sample. Still further, an abnormal cell sample can be prepared by removing selected cells from a cell sample. These removed cells or the cells remaining in the sample may be modified by means known in the art to become an abnormal cell sample. For example, some methods of modifying the cells comprise transforming cells with a retrovirus containing an enzyme by methods known to those skilled in the art, an example of which is disclosed in U.S. Pat. No. 5,443,986 to Haughland et al.

Moreover, an abnormal cell sample can be cultured cells from a selected, established cell line developed from abnormal human leukocytes which can be used to prepare a cell control according to this invention. Cells of the selected cell line are grown in a tissue culture medium using established means, harvested and further processed, if necessary, using clinical or enzymatic procedures to retain the cell's enzyme content. For example, Molt 4, HL-60 and CCRF-CEM cells have been found to have an endogenous abnormal enzymatic activity required for this invention. These cell lines are available from the American Type Culture Collection (ATCC), 10801 University Boulevard, Manassas, Va.

The resulting cell sample can be preserved for use as an enzymatic cell control according to suitable preservation techniques. The cells are typically washed to remove serum plasma growth media and extra cellular enzymes. In a sample production lot, a 1000 ml sample containing $1 \times 10^6$ cells per ml is collected by centrifugation at approximately 200 G force for approximately 10 minutes at approximately 2 to 8° C. The cell pellet is resuspended at approximately $20 \times 10^6$ cell per milliliter (ml) in a physiological buffer solution having an approximate pH from 5 to 9, preferably 6 to 8, such as Hanks buffer or phosphate buffer solution. The resuspended cells are again centrifuged at approximately 200 G force for approximately 10 minutes at approximately 2 to 8° C. The supernatant is decanted and the cell pellet is resuspended for a second time in a physiological buffer solution having an approximate pH from 5 to 9, preferably 6 to 8. The resuspension is again centrifuged at approximately 200 G force for about ten minutes at 2 to 8° C. and the resulting pellet is resuspended for a third time in a physiological buffer solution having an approximate pH from 5 to 9, preferably 6 to 8, at a concentration of approximately $15 \times 10^6$ cell per ml at 2 to 8° C. to form a cell suspension. A carbohydrate carrier, such as Dextran, having a molecular weight of approximately 100,000 to 200,000, preferably 125,000 to 175,000, is solubilized in a separate container at a concentration of approximately 5 to 10, preferably 7 to 8 grams carbohydrate carrier per 100 ml physiological buffer solution having an approximate pH from 5 to 9, preferably 6 to 8, to form a carrier solution.

Next, 80 ml of the carrier solution is placed in a container fitted with an ice bath along with a magnetic stirrer. Then, 20 ml of the cell suspension, which should contain approximately 200 to $400 \times 10^6$ cells, preferably 250 to $350 \times 10^6$ cells, is added to the carrier solution and stirred for approximately 10 minutes to form a lyophilizable cell mixture. Then, approximately 750 microliters of the lyophilizable cell mixture is placed in a vial and partially stoppered with a split rubber stopper. Then, the lyophilizable cell mixture is lyophilized by procedures known to those skilled in the art. The lyophilized vials are removed from the lyophilizer after the lyophilizing cycle is completed and stored at between 2 to 8° C. The lyophilized control cell is checked for quality by performance testing.

For reconstituting, the vial is filled with approximately 750 microliters of distilled water or deionized water. The reconstituted cell control will have an approximate pH from 5 to 9, preferably 6 to 8. To conduct a cell control assay on a flow cytometer, the reconstituted cells are combined with a fluorogenic substrate reagent according to methods prescribed by the reagent manufacturer and thereafter, analyzed by flow cytometer or fluorescence microscopy procedures. In addition, the cell control can be used in other types of enzymatic assays and other suitable diagnostic enzymatic protocols.

The cell control, the method of manufacturing the cell control, and the method of using the cell control can be further understood by reference to the following examples. It will be appreciated, however, that the invention is not limited to the described examples, and that other methods of preparing and using the control cell according to the present invention could be suitable.

EXAMPLE 1

Method for Making a Cytoenzymology Cell Control

Materials:
1. Hanks buffer: 1×, pH 7.4 to 7.55, 275 to 295 milliosmoles (mOsm).
2. CCRF-CEM Cells: $15 \times 1^{06}$ cells per ml in Hanks buffer pH 7.5.
3. Dextran; reagent grade, M.W. 150,000 available from Amresco, Solon, Ohio.
4. Distilled water endotoxin screened.
5. Glass screw cap vial size 2 ml, split rubber stopper, screw cap.
6. Cell Counter, Coulter Corporation Model ZBI or equivalent.
7. pH meter, osmometer, magnetic stirrer, filtration assembly with 0.2 micron filter.
8 Vacuum flask assembly, centrifuge refrigerated, centrifuge bottles.

9. RPMI media, microscope, slides, incubator 37° C. with 5% $CO_2$, Trypan Blue.
10. Glasswares, beakers, flasks, graduate cylinders all sterilized.

Method:

1. Preparation of Hanks buffer: Transfer 100 ml of Hanks 10× stock solution, GIBCO, Gaithersburg, Md. Cat.# 14185-029 to 1 liter Erlenmeyer flask and add 900 ml distilled water reagent grade, GIBCO Cat# 15230-147. Mix with a magnetic stirrer and adjusted the pH from 7.4 to 7.55. If necessary, adjust the pH with 0.1 N HCl or NaOH. Measure the osmolality in an osmometer and should be between 275–295. Filter through 0.2 micron filter and store at 2 to 8° C. in a refrigerator.
2. Cultivation of CCRF-CEM Cells: CCRF-CEM cells are propagated in 90% RPMI 1640 medium and 10% fetal bovine serum. Cultures are maintained by subculturing every 2 to 3 days. The count and viability of the culture are obtained using Trypan Blue to perform the viability count on a microscope. Cultures having a seeding concentration of 0.2 to $0.25 \times 10^6$ viable cells per milliliter will double in approximately 24 hours. A concentration of $1.0 \times 10^6$ per ml is the maximum concentration desired, since cultures with a concentration above this tend to show a lower viability and cell integrity is not as good.
3. Dextran Solution: To prepare 1 liter Dextran solution, transfer 900 ml of Hanks buffer to an Erlenmeyer flask with a magnetic stirrer. Weigh 75 grams of Dextran and add slowly to the Hanks buffer while stirring continuously with a magnetic stirrer. When the solution is complete, transfer to a 1 liter graduate cylinder and adjust the volume to 1 liter with Hanks buffer and mix. Filter the Dextran solution through 0.2 micron filter into a sterile container and store at 2 to 8° C.
4. CCRF-CEM Cell Washing: Transfer CCRF-CEM cells in the growth medium from step 2 to sterile 500 ml centrifuge bottles and centrifuge at 200 G force for about 12 minutes at about 6° C. Discard the supernatant and transfer the pellets from each of the 500 ml bottle to 50 ml sterile plastic centrifuge screw cap tubes and wash twice with cold Hanks buffer solution. Centrifuge at 200 G force for about 10 minutes at approximately 6° C. for each wash cycle. Collect the pellets into a 50 ml centrifuge tube and add about 20 ml Hanks buffer solution, and gently mix and then count the cell population in Coulter ZB-1 or other cell analyzer. Adjust the cell counts to $15 \times 10^6$ cells per ml.
5. CCRF-CEM in Dextran: Place 500 ml sterile plastic bottle with a magnetic stirrer in an ice bath over a magnetic stirrer. Transfer 400 ml Dextran solution from step 3 to the container and start the magnetic stirrer. Slowly add 100 ml CCRF-CEM cells from step 4, which should be approximately $15 \times 10^6$ cells per ml, in a gentle stream into the Dextran solution while stirring at a very slow speed. Continue to stir for additional 10 minutes after the addition of CCRF-CEM cell suspension to the Dextran solution.
6. Lyophilization: The CCRF-CEM cell suspension from step 5 is dispensed into 2 ml vials placed in chilled lyophilizing trays at 750 microliter per vial. Place split rubber stopper partially on the vial and lyophilize as per following program.

| Step | Temp. 0° C. | Vacuum (mm Torr) | Time (min) |
| --- | --- | --- | --- |
| 1 | −40 | 100 | 660 |
| 2 | −15 | 100 | 420 |
| 3 | 10 | 100 | 420 |
| 4 | 25 | 100 | 420 |
| Post Heat | 25 | 100 | 10 |

7. Capping and Labeling: The stoppered vials are capped and then labeled. The vials are stored at 2–8° C. and tested for performance.

The cell control has been successfully used in cytoenzymology examinations with flow cytometry and microscopy methods. The function of the control is to check the efficacy of a reagent in the measurement of cellular activities. The cell control is stable for 8 hours after reconstitution. The cell control is primarily designed for use with the CELLPROBE Reagents sold by Coulter Corporation to measure cellular enzymes in flow cytometry.

EXAMPLE 2

Method of Using a Cytoenzymology Control Cell

1. A vial containing the lyophilized cytoenzymology cell control prepared according to Example 1 is reconstituted with 750 microliters of reagent grade distilled water. The cell control is chilled at 2 to 8° C. for approximately 15 minutes to reach equilibrium. After gentle mixing, 50 microliters of the rehydrated cell control mixture is transferred to a 12×75 mm glass tube.
2. The glass tube is incubated in a 37° C. water bath for about 5 minutes.
3. Add 25 microliters of freshly reconstituted CELLPROBE Reagent to a reaction tube containing the cell control and gently mix and incubate at 37° C. for a time period specified by the reagent manufacturer.
4. Transfer the reaction tube to ice bath and let stand for at least 3 minutes.
5. Add 1 ml ice cold Hanks or PBS buffer to the reaction tube before measuring the fluorescence on a suitable flow cytometer.

In FIGS. 1, 2, and 3, forward scatter (FS) versus side scatter (SS) histograms are shown for a patient whole blood cell sample, the control cell of this invention, and CYTO-TROL® using a CELLPROBE Reagent (Gly-Phe-Gly-Ala)$_2$ Rho110.2TFA. These histograms indicate that the cell control is comparable in morphological characteristics to human lymphocytes obtained from a fresh whole blood sample. More specifically, FIG. 1 shows a whole blood scattergram using FS, SS and the fluorescence intensity of a CELLPROBE Reagent used to monitor a hydrolase enzyme. FIG. 2 shows a cell control of this invention using FS, SS and the fluorescence intensity of a CELLPROBE Reagent used to monitor the same hydrolase enzyme used for the whole blood sample in FIG. 1. FIG. 3 shows a CYTO-TROL® sample using FS, SS and the fluorescence intensity of a CELLPROBE Reagent used to monitor the same hydrolase enzyme used in FIGS. 1 and 2. All instrument settings of PMT, High Voltage and Gain settings for FS, SS and fluorescence measurements were identical for each analysis.

The following table represents the mean channels obtained using twelve CELLPROBE Reagents used to measure hydrolase enzymes with the cell control of this invention and CYTO-TROL® product in the same run. The procedure of Example 1 was followed for each CELLPROBE Reagent.

| CELL PROBE Reagent | Cell Control Mean ch. | CYTO-TROL® Mean Ch. | Human Lymphocytes |
|---|---|---|---|
| (Chloroacetyl)$_2$fluorescein | 4.6 | 0.7 | 2.2 |
| (Palmitate)$_2$fluorescein | 12.6 | 1.5 | 5.5 |
| (Acetate)$_2$fluorescein | 4.0 | 0.4 | 8.4 |
| (Acetate)$_2$fluorescein NaF | 7.6 | 1.8 | 8.6 |
| (Arginine)$_2$Rho110.4TFA | 3.8 | 0.8 | 2.4 |
| (Gly—Pro—Leu—Gly—Pro—Leu)$_2$Rho110.2TFA | 68.1 | 0.9 | 23.3 |
| (Gly—Phe—Gly—Ala)$_2$Rho110.2TFA | 35.9 | 1.6 | 34.3 |
| (Z—Ala—Gly)$_2$Rho110 | 6.8 | 1.4 | 12.0 |
| (Tartrate-Gly—Leu)$_2$ Rho110 | 80.8 | 0.7 | 4.8 |
| (Gly—Gly—Leu)$_2$Rho110.2TFA | 20.8 | 1.3 | 12.3 |
| (Leu—Leu)$_2$Rho110.2TFA | 59.8 | 1.2 | 24.6 |
| Sample Blank | 0.3 | 0.2 | 0.3 |

Wherein the following abbreviations are used:
Ala - Alanine
Gly -Glycine
Leu - Leucine
Phe - Phenylalanine
Pro - Proline
Rho110 - Rhodamine 110
NaF - Sodium fluoride
TFA - Trifluoroacetic acid
Z - Benzyloxycarbonyl

EXAMPLE 3

Method of Using a Cytoenzymology Control Cell

1. The lyophilized cytoenzymology cell control is reconstituted, equilibrated and reacted with a CELL-PROBE Reagent by the method describe in Example 2 above, steps 1, 2, 3, 4 and 5.
2. The reaction tube from Step 5 is centrifuged at 200 G force for 5 minutes at room temperature.
3. The supernatant is removed.
4. One drop, approximately 50 microliters, of the residual cell suspension is smeared evenly with a cover slide and examined under fluorescence microscope.

A photomicrograph of the slide shows both cellular structure and fluorescence contained inside the cell from the hydrolysis of the CELLPROBE Reagent caused by the cellular enzyme.

All patents and publications referred to in this application are hereby incorporated by reference in their entirety.

While in the foregoing specification, a detailed description of the invention has been set down for the purpose of illustration, many variations in the details herein given may be made by those skilled in the art without departing from the spirit and scope of the invention.

The invention has been described with reference to the preferred embodiments. It should be understood, however, that the invention is not so limited, and the scope of the invention should be determined with reference to the following claims, rather than to the foregoing specification.

We claim:

1. A cytoenzymology cell control comprising lyophilized mammalian blood cells selected from Molt-4, CCRF-CEM and HL-60 cells, wherein said lyophilized mammalian cells are capable of being rehydrated in water to function effectively as a cytoenzymology cell control in cytoenzymology analysis by having a hydrolase activity capable of being confirmed by fluorescence analysis, said hydrolase activity being approximately equal to or greater than the hydolase activity of normal human leukocytes and having a cellular structure corresponding to the blood cell prior to lyophilization, said cellular structure capable of being confirmed by light scatter or microscopy analysis.

2. The cytoenzymology cell control of claim 1, wherein said lyophilized mammalian blood cells when rehydrated in water have a pH from 5 to 9.

3. A method of making a cytoenzymology control cell of claim 1 comprising:
   a) forming a cell suspension of a predetermined number of mammalian blood cells selected from Molt-4, CCRF-CEM and HL-60 cells, by suspending said mammalian blood cells in a selected volume of a physiologically acceptable buffer solution,
   b) subjecting the cell suspension to centrifugation to obtain a cell pellet of said mammalian blood cells,
   c) adding the cell pellet to a carbohydrate solution to form a lyophilizable cell suspension, wherein said carbohydrate solution is formed with a carbohydrate having a molecular weight of approximately 100,000 to 200,000, and
   d) lyophilizing said lyophilizable cell suspension.

4. A method of using a cytoenzymology control cell to insure reliability of test results and methods when using a device having means for measuring enzymatic activity comprising:
   a) rehydrating lyophilized mammalian blood cells selected from Molt-4, CCRF-CEM and HL-60 cells, wherein said lyophilized mammalian blood cells are capable of being rehydrated in water to function effectively as a cytoenzymology cell control in flow cytometric analysis, by having a hydrolase activity capable of being confirmed by fluorescence analysis, said hydrolase activity of normal human leukocytes and having a cellular structure corresponding to the blood cell prior to lyophilization, said cellular structure capable of being confirmed by light scatter or microscopy, b) combining a fluorogenic substrate capable of being hydrolyzed by said hydrolase with said rehydrated mammalian blood cells in an instrument capable of detecting fluorescence and cellular structure, and c) analyzing the fluorescence corresponding to the hydrolase activity of said rehydrated mammalian cell control to confirm the reliability of test results and methods when using said device.

5. The method of claim 4, wherein said device is a flow cytometer.

6. The method of claim 5, wherein said rehydrated cell has a pH from 5 to 9.

* * * * *